United States Patent [19]

Gesellchen et al.

[11] 4,351,763
[45] Sep. 28, 1982

[54] PHARMACOLOGICALLY ACTIVE PEPTIDES

[75] Inventors: Paul D. Gesellchen, Indianapolis; Robert T. Shuman, Greenwood, both of Ind.

[73] Assignee: Eli Lilly and Company, Indianapolis, Ind.

[21] Appl. No.: 256,861

[22] Filed: Apr. 24, 1981

Related U.S. Application Data

[62] Division of Ser. No. 104,348, Dec. 17, 1979.

[51] Int. Cl.³ .................. C07C 103/52; A61K 37/00
[52] U.S. Cl. ........................... 260/112.5 E; 424/177
[58] Field of Search ................. 260/112.5 E; 424/177

[56] References Cited

U.S. PATENT DOCUMENTS 4,259,234 3/1981 Smithanck, Jr. et al. ... 260/112.5 R

OTHER PUBLICATIONS

Day et al., Res. Comm. in Chem. Path. and Pharmacol. 14, 597–603 (1976).
Miller et al., Vitamins and Hormones 36, Academic Press, 297–382 (1978).
Coy et al., Biochem. and Biophys. Res. Comm. 83, 997–983 (1978).
Pless et al., "Opiod Activity of Enkephalin Analogues", presented at the 15th European Peptide Symposium, Sep. 4–9, 1978, Gdansk, Poland.
Miller, "Structural Pharmacology and Neurobiology of the Enkephalins and Endorphins", presented at the 176th American Chemical Society National Meeting, Sep. 11–14, 1978, at Miami Beach, Florida.

Primary Examiner—Delbert R. Phillips
Attorney, Agent, or Firm—William C. Martens, Jr.; Arthur R. Whale

[57] ABSTRACT

Compounds of the formula

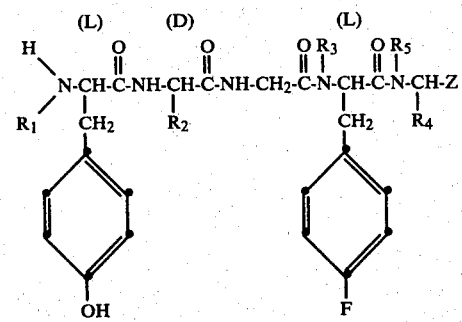

and pharmaceutically acceptable non-toxic acid addition salts thereof, in which
L and D define the chirality;
$R_1$ is hydrogen or $C_1$–$C_3$ primary alkyl;
$R_2$ is $C_1$–$C_4$ primary or secondary alkyl, allyl, cyclopropylmethyl, $C_1$–$C_2$ hydroxyalkyl, or —$(CH_2)_m$-U-$CH_3$ in which U is —S— or

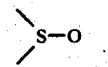

and m is 1 or 2;
$R_3$ is hydrogen, $C_1$–$C_4$ primary or secondary alkyl, cyclopropylmethyl, or allyl;
$R_4$ is hydrogen, $C_1$–$C_5$ primary or secondary alkyl, —$(CH_2)_n$—X—$(CH_2)_p$—$CH_3$ in which X is —O—, —S—,

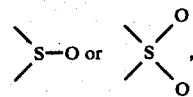

n is 1 or 2, and p is 0 or 1, phenyl, or monosubstituted phenyl in which the substituent is halo, hydroxy, $C_1$–$C_3$ alkoxy, nitro, $C_1$–$C_3$ alkyl, or trifluoromethyl;
$R_5$ is hydrogen or $C_1$–$C_4$ primary alkyl; and
Z is —$CH_2OR_6$,

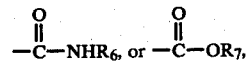

in which $R_6$ is hydrogen or $C_1$–$C_3$ alkyl and $R_7$ is $C_1$–$C_3$ alkyl;
subject to the proviso that one but not both of $R_3$ and $R_5$ is other than hydrogen; are useful analgesic agents.

29 Claims, No Drawings

PHARMACOLOGICALLY ACTIVE PEPTIDES

This application is a division of application Ser. No. 104,348, filed Dec. 17, 1979.

BACKGROUND OF THE INVENTION

This invention relates to a novel class of compounds which exhibit analgesic activity.

Recently, endogenous substances having morphine-like properties have been extracted from mammalian brain or csf. These substances, named enkephalin, have been identified by Hughes et al., *Nature*, 258, 577 (1975) as pentapeptides having the following sequences:

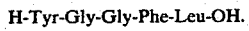

These compounds are referred to as methionine-enkephalin and leucine-enkephalin, respectively.

Although methionine and leucine enkephalin have been shown to exhibit analgesic activity in mice upon administration intracerebroventricularly [Buscher et al., *Nature*, 261, 423 (1976)], they are practically devoid of any useful analgesic activity when administered parenterally.

Therefore, since the discovery of the enkephalins, much effort has been devoted to preparing analogs of the enkephalins in the hope of finding compounds having enhanced activity and practical utility due to their bioavailability by parenteral or oral administration.

Dutta et al., *Life Sciences* 21, pp. 559-562 (1977) report certain structure modifications which, they suggest, tend to enhance potency. They suggest activity can be enhanced by any or all of the following:

(a) substitution of Gly in position 2 by certain D- or α-aza-amino acids;

(b) conversion of the terminal carboxyl to the methyl ester or the amide;

(c) modification of the Phe in the 4-position by α-aza substitution, N-methylation, or hydrogenation of the aromatic ring.

In addition, Roemer et al., *Nature* 268, pp. 547-549 (1977), suggest modification of the Met[5] to its corresponding carbinol and oxidation of the Met sulfur to the sulfoxide as useful modifications.

Another structure modification of significance is that reported in Belgian Pat. No. 859,026. This publication suggests enhancement of activity and bioavailability of enkephalin analogs by insertion of a D-amino acid residue in position 2, conversion of the terminal carboxyl to an amide, and N-alkylation of the amino acid residue in position 5.

A class of analogs of enkephalin having a high level of analgesic activity has now been discovered. These analogs are halogenated enkephalins which are structurally highly specific in terms both of the identity and the position of the halogen. The compounds of this invention are pentapeptides having the residue of a p-fluoro-substituted L-phenylalanine in the 4-position of the peptide.

The literature recognizes other halogenated 4-phenylalanyl enkephalin analogs; however, none are mono p-fluoro-substituted 4-phenylalanyl enkephalin analogs. A. R. Day et al., *Res. Comm. in Chem. Path. and Pharmacol.* 14 (4), 597-603 (1976) reports H-Tyr-Gly-Gly-pClPhe-Nle-OH. R. J. Miller et al., *Vitamins and Hormones* 36, 297-382, Academic Press (1978) mentions H-Tyr-D-Ala-Gly-pClPhe-D-Leu-OH; H-Tyr-D-Ala-Gly-pClPhe-D-Leu-OMe; and H-Tyr-D-Ala-Gly-pClPhe-D-Leu-NHEt. Pless et al., "Opioid Activity of Enkephalin Analogues," presented at the 15th European Peptide Symposium, Sept. 4-9, 1978, Gdansk, Poland, reports H-Tyr-D-Ala-Gly-pClPhe-Met(O)-OL. D. H. Coy et al., *BBRC* 83 (3), 977-983 (1978) mentions H-Tyr-D-Ala-Gly-F$_5$-Phe-Met-NH$_2$.

None of the above reports the compounds of this invention, and it has been discovered that both the identity and position of the halogen play a significant role in the level of analgesic activity of the enkephalin analog.

SUMMARY OF THE INVENTION

Thus, this invention relates to a class of compounds having the formula

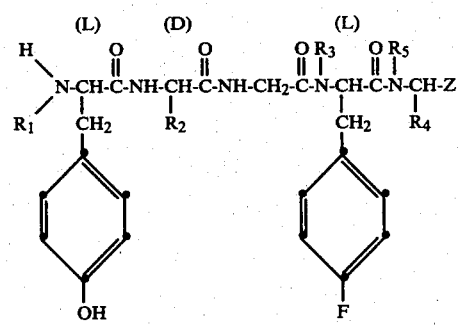

and pharmaceutically acceptable non-toxic acid addition salts thereof, in which L and D define the chirality;

$R_1$ is hydrogen or $C_1-C_3$ primary alkyl;

$R_2$ is $C_1-C_4$ primary or secondary alkyl, allyl, cyclopropylmethyl, $C_1-C_2$ hydroxyalkyl, or —(CH$_2$)$_m$—U—CH$_3$ in which U is —S— or

and m is 1 or 2;

$R_3$ is hydrogen, $C_1-C_4$ primary or secondary alkyl, cyclopropylmethyl, or allyl;

$R_4$ is hydrogen, $C_1-C_5$ primary or secondary alkyl, —(CH$_2$)$_n$-X-(CH$_2$)$_p$—CH$_3$ in which X is —O—, —S—,

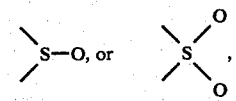

n is 1 or 2, and p is 0 or 1, phenyl, or monosubstituted phenyl in which the substituent is halo, hydroxy, $C_1-C_3$ alkoxy, nitro, $C_1-C_3$ alkyl, or trifluoromethyl;

$R_5$ is hydrogen or $C_1-C_4$ primary alkyl; and

Z is —CH$_2$OR$_6$,

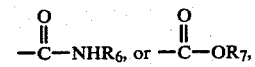

in which R$_6$ is hydrogen or $C_1-C_3$ alkyl and R$_7$ is $C_1-C_3$ alkyl;

subject to the proviso, that, when one of R$_3$ and R$_5$ is other than hydrogen, the other is hydrogen.

DETAILED DESCRIPTION OF THE INVENTION

As indicated above, the compounds of this invention have the following structure:

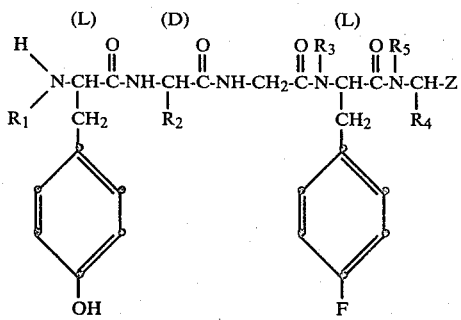

Also included are the pharmaceutically acceptable non-toxic acid addition salts of these compounds.

Pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salts are those prepared from hydrochloric acid, acetic acid, or succinic acid. Any of the above salts are prepared by conventional methods.

As will be noted from the definition of the various substituents which appear in the above structure, the compounds which are defined by this structure are pentapeptides, the C-terminal portion of which is a primary alcohol or its lower alkyl ether derivative, a primary or secondary amide, or a lower alkyl ester.

The stereoconfiguration of the compounds of this invention is an essential feature thereof. For the sake of convenience, the amino acid residues of the pentapeptides of this invention are numbered sequentially beginning with the residue at the terminal amino function. The chirality of the amino acid residues, reading from Position 1 through Position 4, is L, D, none, and L. The residue in Position 3 is a glycine moiety, and, thus, no chirality as to this residue exists. As to Position 5 (the C-terminal position), its chirality is defined as that which is consistent with and corresponds to the corresponding putative L-amino acid residue or the corresponding putative D-amino acid residue, as well as, of course, the racemic mixture of both.

The group $R_1$ as used herein is defined to include the group "$C_1$-$C_3$ primary alkyl". By the term "$C_1$-$C_3$ primary alkyl" is meant methyl, ethyl, and n-propyl.

The groups $R_6$ and $R_7$ as used herein are defined to include the group "$C_1$-$C_3$ alkyl". By the term "$C_1$-$C_3$ alkyl" is intended methyl, ethyl, n-propyl and isopropyl.

The group $R_5$ as used herein is defined to include the group "$C_1$-$C_4$ primary alkyl". By the term "$C_1$-$C_4$ primary alkyl" is intended methyl, ethyl, n-propyl, and n-butyl.

The groups $R_2$ and $R_3$ appearing in the above structural formula are defined to include the group "$C_1$-$C_4$ primary or secondary alkyl". By the term "$C_1$-$C_4$ primary or secondary alkyl" is meant methyl, ethyl, n-propyl, isopropyl, n-butyl, isobutyl, and sec-butyl.

The group $R_4$ appearing in the above structural formula is defined to include the group "$C_1$-$C_5$ primary or secondary alkyl." By the term "$C_1$-$C_5$ primary or secondary alkyl" is meant methyl, ethyl, n-propyl, isopropyl, n-butyl, isobutyl, sec-butyl, n-pentyl, isopentyl, 2-methylbutyl, and neo-pentyl.

The group $R_2$ is also defined as "$C_1$-$C_2$ hydroxyalkyl". By the term "$C_1$-$C_2$ hydroxyalkyl" is meant hydroxymethyl, 1-hydroxyethyl, and 2-hydroxyethyl.

The group $R_2$ appearing in the above structural formula is defined to include the group —$(CH_2)_m$—U—$CH_3$ in which U is —S— or

and m is 1 or 2. By the term "—$(CH_2)_m$—U—$CH_3$" is meant methylthiomethyl, methylthioethyl, and the sulfoxides of both.

The group $R_4$ appearing in the above structural formula is defined to include the group —$(CH_2)_n$—X—$(CH_2)_p$—$CH_3$ in which X is —O—, —S—,

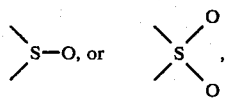

n is 1 or 2, and p is 0 or 1. By the term "—$(CH_2)_n$—X—$(CH_2)_p$—$CH_3$" is meant methylthiomethyl, ethylthiomethyl, methylthioethyl, ethylthioethyl, and the sulfoxides and sulfones of each, as well as methoxymethyl, ethoxymethyl, methoxyethyl and ethoxyethyl. The term "halo" as used herein includes fluoro, chloro, bromo, and iodo. The term "$C_1$-$C_3$ alkoxy" as used herein includes methoxy, ethoxy, propoxy, and isopropoxy.

The group $R_4$ is defined to include mono-substituted phenyl, the substituent of which is halo, hydroxy, $C_1$-$C_3$ alkoxy, nitro, $C_1$-$C_3$ alkyl, or trifluoromethyl. Illustrations of these substituted phenyl moieties are p-chlorophenyl, p-fluorophenyl, m-bromophenyl, p-iodophenyl, o-chlorophenyl, p-hydroxyphenyl, o-hydroxyphenyl, p-methoxyphenyl, m-ethoxyphenyl, o-methoxyphenyl, m-propoxyphenyl, p-isopropoxyphenyl, p-nitrophenyl, m-nitrophenyl, p-tolyl, m-tolyl, o-ethylphenyl, p-cumyl, m-cumyl, p-propylphenyl, p-ethylphenyl, p-trifluoromethylphenyl, m-trifluoromethylphenyl, and the like.

With respect to the particular position residues of the pentapeptides of this invention, the following considerations prevail:

(A) Position 1

This position represents the amino-terminal portion of the peptide. The residue is that which results from L-tyrosine. The residue can be N-unsubstitued, in which case $R_1$ is hydrogen. Moreover, the residue can be substituted by a $C_1$-$C_3$ primary alkyl, giving rise to N-methyl-, N-ethyl-, or N-n-propyl-. For compounds having exceptionally high levels of analgesic activity when administered parenterally, the tyrosyl residue which is present in Position 1 preferably is N-unsubstituted. For compounds having exceptionally high levels of analgesic activity when administered orally, the tyrosyl residue which is present in Position 1 preferably is N-substituted. In the event that the tyrosyl is N-substituted, the N-substituent preferably is methyl.

(B) Position 2

The amino acid residue which is present in the second position of the peptide of this invention must be the D stereoisomer and is any of several amino acid residues. These include residues derived from D-alanine (Ala) ($R_2$ is methyl), D-α-aminobutyric acid (Abu) ($R_2$ is ethyl), D-norvaline (Nva) ($R_2$ is n-propyl), D-valine (Val) ($R_2$ is isopropyl), D-norleucine (Nle) ($R_2$ is n-butyl), D-leucine (Leu) ($R_2$ is isobutyl), D-isoleucine (Ile) ($R_2$ is sec-butyl), D-allylglycine [gly(Al)] ($R_2$ is allyl), D-cyclopropylmethylglycine [Gly(Cp)] ($R_2$ is cyclopropylmethyl), D-methionine (Met) ($R_2$ is 2-methylthioethyl), D-(S-methyl)cysteine [Cys(Me)] ($R_2$ is methylthiomethyl), D-methionine sulfoxide [Met(O)] ($R_2$ is methylsulfinylethyl), D-(S-methyl)cysteine sulfoxide [Cys(Me)(O)] ($R_2$ is methylsulfinylmethyl), D-serine (Ser) ($R_2$ is hydroxymethyl), D-threonine (Thr) ($R_2$ is 1-hydroxyethyl), and D-homoserine (Hse) ($R_2$ is 2-hydroxyethyl). Preferably, $R_2$ is $C_1$-$C_4$ primary or secondary alkyl or $C_1$-$C_2$ hydroxyalkyl. Of the two groups, $C_1$-$C_4$ primary or secondary alkyl is more preferred, and of the latter, the residue derived from D-alanine.

(C) Position 3

The amino acid residue present in this position is that derived from glycine (Gly).

(D) Position 4

The amino acid residue present in this position is that derived from p-fluoro substituted L-phenylalanine [Phe(F)]. The residue can be either unsubstituted or substituted at the amino nitrogen ($R_3$). In the event that the residue is N-substituted, it is N-methyl, N-ethyl, N-n-propyl, N-isopropyl, N-n-butyl, N-isobutyl, N-sec-butyl, N-cyclopropylmethyl, or N-allyl. Preferably, when $R_3$ is other than hydrogen, it is $C_1$-$C_4$ primary or secondary alkyl, and, if the latter, methyl or ethyl.

(E) Position 5

The residue present in the C-terminal position of the compounds of this invention is an amino acid structurally derivatized to its amide (Z is

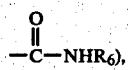

its primary alcohol or corresponding $C_1$-$C_3$ alkyl ether (Z is -$CH_2OR_6$), or its $C_1$-$C_3$ alkyl ester (Z is

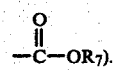

The chirality of the amino acid residue in Position 5 of the pentapeptide is the L-, the D-, or the D,L-mixture. Preferably, the chirality of the amino acid residue is L-. The residue is represented by any of the following, each of which has been derivatized to its amide, its primary alcohol ether, or its ester. These include glycine (Gly) ($R_4$ is hydrogen), alanine (Ala) ($R_4$ is methyl), α-aminobutyric acid (Abu) ($R_4$ is ethyl), norvaline (Nva) ($R_4$ is n-propyl), valine (Val) ($R_4$ is isopropyl), norleucine (Nle) ($R_4$ is n-butyl), leucine (Leu) ($R_4$ is isobutyl), isoleucine (Ile) ($R_4$ is sec-butyl), α-aminoheptanoic acid (Ahp) ($R_4$ is n-pentyl), homoleucine (Hle) ($R_4$ is isopentyl), homoisoleucine (Hil) ($R_4$ is 2-methylbutyl), neopentylglycine (Npg) ($R_4$ is neopentyl), phenylglycine (Pgl) ($R_4$ is phenyl), p-hydroxyphenylglycine [Pgl(OH)] ($R_4$ is p-hydroxyphenyl), (S-methyl)cysteine [Cys(Me)] ($R_4$ is methylthiomethyl), (S-methyl)cysteine sulfoxide [Cys(Me)(O)] ($R_4$ is methylsulfinylmethyl), (S-methyl)cysteine sulfone [Cys(Me)($O_2$)] ($R_4$ is methylsulfonylmethyl), (S-ethyl)cysteine [Cys(Et)] ($R_4$ is ethylthiomethyl), (S-ethyl)cysteine sulfoxide [Cys(Et)(O)] ($R_4$ is ethylsulfinylmethyl), (S-ethyl)cysteine sulfone [Cys(Et)($O_2$)] ($R_4$ is ethylsulfonylmethyl), methionine (Met) ($R_4$ is methylthioethyl), methionine sulfoxide [Met(O)] ($R_4$ is methylsulfinylethyl), methionine sulfone [Met($O_2$)] ($R_4$ is methylsulfonylethyl), ethionine (Eth) ($R_4$ is ethylthioethyl), ethionine sulfoxide [Eth(O)] ($R_4$ is ethylsulfinylethyl), ethionine sulfone [Eth($O_2$)] ($R_4$ is ethylsulfonylethyl), (O-methyl)serine [Ser(Me)] ($R_4$ is methoxymethyl), (O-ethyl)serine [Ser(Et)] ($R_4$ is ethoxymethyl), (O-methyl)homoserine [Hse(Me)] ($R_4$ is methoxyethyl), and (O-ethyl)homoserine [Hse(Et)] ($R_4$ is ethoxyethyl).

A preferred class of compounds are those in which $R_4$ is $C_1$-$C_5$ primary or secondary alkyl. Of the latter compounds which are highly preferred are those in which $R_4$ is $C_4$ primary or secondary alkyl, and, in particular, isobutyl, which defines the leucine residue.

Another preferred class are those compounds in which $R_4$ is —$(CH_2)_n$-X-$(CH_2)_p$—$CH_3$. Of these, methylthioethyl, which defines methionine, is highly preferred.

Another preferred class are those compounds in which $R_5$ is hydrogen and $R_4$ is phenyl or p-hydroxyphenyl.

The residue of this terminal amino acid is either unsubstituted or substituted at its amino nitrogen ($R_5$). In those instances in which a substituent is present, the substituent is a $C_1$-$C_4$ primary alkyl group. The represented substituents are N-methyl, N-ethyl, N-n-propyl, and N-n-butyl. Preferably, the amino nitrogen is substituted, i.e., $R_5$ is $C_1$-$C_4$ primary alkyl. More preferably, the primary alkyl is methyl. Furthermore, when $R_5$ is other than hydrogen, $R_3$ must be hydrogen, and when $R_3$ is other than hydrogen, $R_5$ must be hydrogen.

In addition, as already noted, the residue in Position 5 is an amide, a primary alcohol, an ether, or an ester. Preferably, the residue is an amide, an alcohol, or an ester, and, more preferably, is an amide. Of the latter, the residue preferably is a primary amide, i.e., Z is a primary amide, i.e., Z is

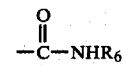

and $R_6$ is hydrogen. When the amide is a secondary amide, $R_6$ is a $C_1$-$C_3$ alkyl group. In those instances, the terminal amide group is N-methyl, N-ethyl, N-n-propyl, or N-isopropyl, and, preferably, is N-methyl.

In this specification, the following abbreviations, most of which are well known and are commonly used in the art, are employed:

Abu: α-aminobutyric acid
Ahp: α-aminoheptanoic acid
Ala: alanine
Cys: cysteine
Cys(Et): (S-ethyl)cysteine
Cys(Et): (O) (S-ethyl)cysteine sulfoxide
Cys(Et): ($O_2$) (S-ethyl)cysteine sulfone Cys(Me): (S-methyl)cysteine
Cys(Me) (O): (S-methyl)cysteine sulfoxide
Cys(Me) (O$_2$): (S-methyl)cysteine sulfone
Eth: ethionine
Eth(O): ethionine sulfoxide
Eth(O$_2$): ethionine sulfone
Gly: glycine
Gly(Al): allylglycine
Gly(Cp): cyclopropylmethylglycine
Hil: homoisoleucine
Hle: homoleucine
Hse: homoserine
Hse(Me): (O-methyl)homoserine
Hse(Et): (O-ethyl)homoserine
Ile: isoleucine
Leu: leucine
Met: methionine
Met(O): methionine sulfoxide
Met(O$_2$): methionine sulfone
Nle: norleucine
Npg: neopentylglycine
Nva: norvaline
Pgl: phenylglycine
Pgl(OH): p-hydroxyphenylglycine
Phe: phenylalanine
Phe(F): p-fluorophenylalanine
Ser: serine
Ser(Me): (O-methyl)serine
Ser(Et): (O-ethyl)serine
Thr: threonine
Tyr: tyrosine
Val: valine
Ac: acetyl
Al: allyl
Cp: cyclopropylmethyl
Me: methyl
Et: ethyl
Ip: isopropyl
Pr: n-propyl
Bu: n-butyl
i-Bu: isobutyl
t-Bu: t-butyl
s-Bu: sec-butyl
Boc: t-butyloxycarbonyl
Bzl: benzyl
Cbz: benzyloxycarbonyl
DCC: N,N'-dicyclohexylcarbodiimide
HBT: 1-hydroxybenzotriazole
DMF: N,N-dimethylformamide
TFA: trifluoroacetic acid
THF: tetrahydrofuran
DEAE: diethylaminoethyl
IBCF: isobutyl chloroformate
NMM: N-methylmorpholine
18-crown-6 1,4,7,10,13,16-hexaoxacyclooctadecane Examples of typical compounds of this invention include the following:

H-L-Tyr-D-Ala-Gly-L-(N-Me)Phe(F)-L-Met-NH$_2$;
H-L-Tyr-D-Ala-Gly-L-Phe(F)-L-(N-Me)Met-NH$_2$;
H-L-Tyr-D-Abu-Gly-L-Phe(F)-L-(N-Et)Met-NH$_2$;
H-L-Tyr-D-Abu-Gly-L-Phe(F)-D-(N-Me)Met-NH$_2$;
H-L-Tyr-D-Nva-Gly-L-Phe(F)-L-(N-Me)Met-NH$_2$;
H-L-Tyr-D-Nva-Gly-L-(N-Et)Phe(F)-L-Met-NH$_2$;
H-L-Tyr-D-Val-Gly-L-Phe(F)-D-(N-Et)Met-NH$_2$;
H-L-Tyr-D-Val-Gly-L-(N-Pr)Phe(F)-L-Met-NH$_2$;
H-L-Tyr-D-Nle-Gly-L-Phe(F)-L-(N-Bu)Met-NH$_2$;
H-L-Tyr-D-Nle-Gly-L-Phe(F)-D-(N-Et)Gly-NH$_2$;
H-L-Tyr-D-Leu-Gly-L-(N-Ip)Phe(F)-L-Met-NH$_2$;
H-L-Tyr-D-Leu-Gly-L-Phe(F)-L-(N-Pr)Met-NH$_2$;
H-L-Tyr-D-Ile-Gly-L-Phe(F)-L-(N-Bu)Met-NH$_2$;
H-L-Tyr-D-Ile-Gly-L-Phe(F)-D-(N-Pr)Met-NH$_2$;
H-L-Tyr-D-Ala-Gly-L-Phe(F)-L-(N-Et)Met-NH$_2$;
H-L-Tyr-D-Ala-Gly-L-Phe(F)-L-(N-Pr)Met-NH$_2$;
H-L-Tyr-D-Ala-Gly-L-Phe(F)-D-(N-Pr)Met-NH$_2$;
H-L-Tyr-D-Ala-Gly-L-(N-i-Bu)Phe(F)-L-Met-NH$_2$;
H-L-Tyr-D-Ala-Gly-L-Phe(F)-L-(N-Bu)Met-NH$_2$;
H-L-Tyr-D-Ala-Gly-L-(N-s-Bu)Phe(F)-D-Met-NH$_2$;
H-L-Tyr-D-Ala-Gly-L-Phe(F)-L-(N-Me)Ala-NH$_2$;
H-L-Tyr-D-Ala-Gly-L-Phe(F)-L-(N-Me)Abu-NH$_2$;
H-L-Tyr-D-Ala- Gly-L-Phe(F)-L-(N-ET)Nva-NH$_2$;
H-L-Tyr-D-Ala-Gly-L-Phe(F)-D-(N-Et)Val-NH$_2$;
H-L-Tyr-D-Val-Gly-L-Phe(F)-L-(N-Me)Nle-NH$_2$;
H-L-Tyr-D-Leu-Gly-L-Phe(F)-L-(N-Me)-Leu-NH$_2$;
H-L-Tyr-D-Val-Gly-L-Phe(F)-L-(N-Et)Ile-NH$_2$;
H-L-Tyr-D-Leu-Gly-L-Phe(F)-D-(N-Me)Ahp-NH$_2$;
H-L-Tyr-D-Ala-Gly-L-(N-Cp)Phe(F)-L-Nle-NH$_2$;
H-L-Tyr-D-Ala-Gly-L-Phe(F)-L-(N-Et)Hse(Me)-NH$_2$;
H-L-Tyr-Ala-Gly-L-Phe(F)-L-(N-Me)Hle-NH$_2$;
H-L-Tyr-D-Ala-Gly-L-Phe(F)-D-(N-Me)Hse(Me)-NH$_2$;
H-L-Tyr-D-Ala-Gly-L-(N-Al)Phe(F)-L-Met-NH$_2$;
H-L-Tyr-D-Gly(Al)-Gly-L-Phe(F)-L-(N-Me)Met-NH$_2$;
H-L-Tyr-D-Gly(Cp)-Gly-L-Phe(F)-L-(N-Me)Hil-NH$_2$;
H-L-Tyr-D-Met-Gly-L-Phe(F)-L-(N-Me)Met-NH$_2$;
H-L-Tyr-D-Cys(Me)-Gly-L-Phe(F)-D-(N-Et)Met-NH$_2$;
H-L-Tyr-D-Met(O)-Gly-L-Phe(F)-L-(N-Et)Met-NH$_2$;
H-L-Tyr-D-Cys(Me) (O)-Gly-L-Phe(F)-L-(N-Me)Npg-NH$_2$;
H-L-Tyr-D-Ser-Gly-L-Phe(F)-L-(N-Me)Hse(Me)-NH$_2$;
H-L-Tyr-D-Ala-Gly-L-(N-Et)-Phe(F)-L-Pgl-NH$_2$;
H-L-Tyr-D-Ala-Gly-L-Phe(F)-L-(N-Me)Pgl(OH)-NH$_2$;
H-L-Tyr-D-Thr-Gly-L-(N-Et)Phe(F)-L-Met-NH$_2$;
H-L-Tyr-D-Hse-Gly-L-Phe(F)-L-(N-Me)Met-NH$_2$;
(N-Me)-L-Tyr-D-Ala-Gly-L-Phe(F)-L-(N-Me)-Cys(-Me)-NH$_2$;
H-L-Tyr-D-Ala-Gly-L-Phe(F)-L-(N-Me)-Cys(Me)-(O)-NH$_2$;
H-L-Tyr-D-Ala-Gly-L-Phe(F)-D-(N-Me)Cys(Et)-NH$_2$;
(N-Et)-L-Tyr-D-Abu-Gly-L-Phe(F)-L-(N-Et)-Nle-NH$_2$;
H-L-Tyr-D-Val-Gly-L-(N-Et)Phe(F)-L-Hse(Me)-NH$_2$;
(N-Pr)-L-Tyr-D-Leu-Gly-L-Phe(F)-L-(N-Me)-Cys(Et)(O$_2$)-NH$_2$;
H-L-Tyr-D-Abu-Gly-L-Phe(F)-L-(N-Pr)Met(O)-NH$_2$;
H-L-Tyr-D-Nle-Gly-L-Phe(F)-L-(N-Me)Eth-NH$_2$;
H-L-Tyr-D-Ile-Gly-L-Phe(F)-D-(N-Pr)Eth(O)-NH$_2$;
(N-Me)-L-Tyr-D-Leu-Gly-L-Phe(F)-L-(N-Et)-Nle-NH$_2$;
(N-Me)-L-Tyr-D-Nva-Gly-L-Phe(F)-L-(N-Me)Hse(Et)-NH$_2$;
(N-Me)-L-Tyr-D-Ala-Gly-L-(N-Et)-Phe(F)-D-Ser(-Me)-NH$_2$;
H-L-Tyr-D-Ala-Gly-L-(N-Me)Phe(F)-L-Ser(Et)-NH$_2$;
H-L-Tyr-D-Ala-Gly-L-(N-Me)Phe(F)-D-Leu-NH$_2$;
H-L-Tyr-D-Ala-Gly-L-(N-Et)Phe(F)-L-Pgl-NH$_2$;
H-L-Tyr-D-Ala-Gly-L-(N-Al)Phe(F)-L-Leu-NH$_2$;
H-L-Tyr-D-Ala-Gly-L-(N-Pr)Phe(F)-L-Pgl(OH)-NH$_2$;
H-L-Tyr-D-Ala-Gly-L-(N-Me)Phe(F)-L-Met-NH$_2$;
H-L-Tyr-D-Ala-Gly-L-(N-Et)Phe(F)-L-Met(O$_2$)-NH$_2$;
H-L-Tyr-D-Ala-Gly-L-(N-Et)Phe(F)-L-Met-NH(Me);

H-L-Tyr-D-Ala-Gly-L-Phe(F)-L-(N-Me)Met-NH(Me);
H-L-Tyr-D-Ala-Gly-L-Phe(F)-L-(N-Et)Met-NH(Me);
H-L-Tyr-D-Ala-Gly-L-Phe(F)-L-(N-Me)Met-NH(Et);
H-L-Tyr-D-Ala-Gly-L-(N-Et)Phe(F)-L-Met-NH(Et);
H-L-Tyr-D-Ala-Gly-L-Phe(F)-L-(N-Me)-Nle-NH(Me);
H-L-Tyr-D-Ala-Gly-L-Phe(F)-L-(N-Et)Pgl-NH(Pr);
H-L-Tyr-D-Ala-Gly-L-Phe(F)-L-(-Pr)Leu-NH(Me);
H-L-Tyr-D-Ala-Gly-L-(N-Al)Phe(F)-L-Met-NH(Ip);
H-L-Tyr-D-Ala-Gly-L-(N-Me)Phe(F)-L-Met-CH$_2$OH;
H-L-Tyr-D-Ala-Gly-L-Phe(F)-L-(N-Me)Met-CH$_2$OH;
H-L-Tyr-D-Abu-Gly-L-Phe(F)-L-(N-Et)Met-CH$_2$OH;
H-L-Tyr-D-Abu-Gly-L-Phe(F)-D-(N-Me)Met-CH$_2$OH;
H-L-Tyr-D-Nva-Gly-L-Phe(F)-L-(N-Me)Met-CH$_2$OH;
H-L-Tyr-D-Nva-Gly-L-(N-Et)Phe(F)-L-Met-CH$_2$OH;
H-L-Tyr-D-Val-Gly-L-Phe(F)-D-(N-Et)Met-CH$_2$OH;
H-L-Tyr-D-Val-Gly-L-(N-Pr)Phe(F)-L-Met-CH$_2$OH;
H-L-Tyr-D-Nle-Gly-L-Phe(F)-L-(N-Bu)Met-CH$_2$OH;
H-L-Tyr-D-Nle-Gly-L-Phe(F)-D-(N-Et)Gly-CH$_2$OH;
H-L-Tyr-D-Leu-Gly-L-(N-Ip)Phe(F)-L-Met-CH$_2$OH;
H-L-Tyr-D-Leu-Gly-L-Phe(F)-L-(N-Pr)Met-CH$_2$OH;
H-L-Tyr-D-Ile-Gly-L-Phe(F)-L-(N-Bu)Met-CH$_2$OH;
H-L-Tyr-D-Ile-Gly-L-Phe(F)-D-(N-Pr)Met-CH$_2$OH;
H-L-Tyr-D-Ala-Gly-L-Phe(F)-L-(N-Et)Met-CH$_2$OH;
H-L-Tyr-D-Ala-Gly-L-Phe(F)-L-(N-Pr)Met-CH$_2$OH;
H-L-Tyr-D-Ala-Gly-L-Phe(F)-D-(N-Pr)Met-CH$_2$OH;
H-L-Tyr-D-Ala-Gly-L-(N-i-Bu)Phe(F)-L-Met-(O$_2$)-CH$_2$OH;
H-L-Tyr-D-Ala-Gly-L-Phe(F)-L-(N-Bu)Met-CH$_2$OH;
H-L-Tyr-D-Ala-Gly-L-(N-s-Bu)Phe(F)-D-Met-CH$_2$OH;
H-L-Tyr-D-Ala-Gly-L-Phe(F)-L-(N-Me)Ala-CH$_2$OH;
H-L-Tyr-D-Ala-Gly-L-Phe(F)-L-(N-Me)Abu-CH$_2$OH;
H-L-Tyr-D-Ala-Gly-L-Phe(F)-L-(N-Et)Nva-CH$_2$OH;
H-L-Tyr-D-Ala-Gly-L-Phe(F)-D-(N-Et)Val-CH$_2$OH;
H-L-Tyr-D-Val-Gly-L-Phe(F)-L-(N-Me)Nle-CH$_2$OH;
H-L-Tyr-D-Leu-Gly-L-Phe(F)-L-(N-Me)Leu-CH$_2$OH;
H-L-Tyr-D-Val-Gly-L-Phe(F)-L-(N-Et)Ile-CH$_2$OH;
H-L-Tyr-D-Leu-Gly-L-Phe(F)-D-(N-Me)Ahp-CH$_2$OH;
H-L-Tyr-D-Ala-Gly-L-(N-Cp)Phe(F)-L-Nle-CH$_2$OH;
H-L-Tyr-D-Ala-Gly-L-Phe(F)-L-(N-Et)Hse(Me)-CH$_2$OH;
H-L-Tyr-D-Ala-Gly-L-Phe(F)-L-(N-Me)Hle-CH$_2$OH;
H-L-Tyr-D-Ala-Gly-L-Phe(F)-D-(N-Me)Hse(Me)-CH$_2$OH;
H-L-Tyr-D-Ala-Gly-(N-Al)Phe(F)-L-Met-CH$_2$OH;
H-L-Tyr-D-Gly(Al)-Gly-L-Phe(F)-L-(N-Me)Met-CH$_2$OH;
H-L-Tyr-D-Gly(Cp)-Gly-L-Phe(F)-L-(N-Me)Hil-CH$_2$OH;
H-L-Tyr-D-Met-Gly-L-Phe(F)-L-(N-Me)Met-CH$_2$OH;
H-L-Tyr-D-Cys(Me)-Gly-L-Phe(F)-D-(N-Et)Met-CH$_2$OH;
H-L-Tyr-D-Met(O)-Gly-L-Phe(F)-L-(N-Et)Met-CH$_2$OH;
H-L-Tyr-D-Cys(Me) (O)-Gly-L-Phe(F)-L-(N-Me)Npg-CH$_2$OH;
H-L-Tyr-D-Ser-Gly-L-Phe(F)-L-(N-Me)Hse(Me)-CH$_2$OH;
H-L-Tyr-D-Ala-Gly-L-(N-Et)-Phe(F)-L-Pgl-CH$_2$OH;
H-L-Tyr-D-Ala-Gly-L-Phe(F)-L-(N-Me)Pgl(OH)-CH$_2$OH;
H-L-Tyr-D-Thr-Gly-L-Phe(F)-L-(N-Et)Phe(F)-L-Met-CH$_2$OH;
H-L-Tyr-D-Hse-Gly-L-Phe(F)-L-(N-Me)Met-CH$_2$OH;
(N-Me)-L-Tyr-D-Ala-Gly-L-Phe(F)-L-(N-Me)Cys(Me)-CH$_2$OH;
H-L-Tyr-D-Ala-Gly-L-Phe(F)-L-(N-Me)-Cys(Me)(O)-CH$_2$OH;
H-L-Tyr-D-Ala-Gly-L-Phe(F)-D-(N-Me)Cys(Et)-(O$_2$)-CH$_2$OH;
(N-Et)-L-Tyr-D-Abu-Gly-L-Phe(F)-L-(N-Et)-Nle-CH$_2$OH;
H-L-Tyr-D-Val-Gly-L-(N-Et)Phe(F)-L-Hse(Me)-CH$_2$OH;
(N-Pr)-L-Tyr-D-Leu-Gly-L-Phe(F)-L-(N-Me)Cys(Et)-(O)-CH$_2$OH;
H-L-Tyr-D-Abu-Gly-L-Phe(F)-L-(N-Pr)Met(O)-CH$_2$OH;
H-L-Tyr-D-Nle-Gly-L-Phe(F)-L-(N-Me)Eth-CH$_2$OH;
H-L-Tyr-D-Ile-Gly-L-Phe(F)-D-(N-Pr)Eth(O$_2$)-CH$_2$OH;
(N-Me)-L-Tyr-D-Leu-Gly-L-Phe(F)-L-(N-Et)-Nle-CH$_2$OH;
(N-Me)-L-Tyr-D-Nva-Gly-L-Phe(F)-L-(N-Me)Hse(Et)-CH$_2$OH;
(N-Me)-L-Tyr-D-Ala-Gly-L-(N-Et)Phe(F)-D-Ser(Me)-CH$_2$OH;
H-L-Tyr-D-Ala-Gly-L-(N-Me)Phe(F)-L-Ser(Et)-CH$_2$OH;
H-L-Tyr-D-Ala-Gly-L-(N-Me)Phe(F)-D-Leu-CH$_2$OH;
H-L-Tyr-D-Ala-Gly-L-(N-Et)Phe(F)-L-Pgl-CH$_2$OH;
H-L-Tyr-D-Ala-Gly-L-(N-Al)Phe(F)-L-Leu-CH$_2$OH;
H-L-Tyr-D-Ala-Gly-L-(N-Pr)Phe(F)-L-Pgl(OH)-CH$_2$OH;
H-L-Tyr-D-Ala-Gly-L-(N-Me)Phe(F)-L-Met-CH$_2$OH;
H-L-Tyr-D-Ala-Gly-L-(N-Et)Phe(F)-L-Met(O)-CH$_2$OH;
H-L-Tyr-D-Ala-Gly-L-(N-Et)Phe(F)-L-Met-CH$_2$OMe;
H-L-Tyr-D-Ala-Gly-L-Phe(F)-L-(N-Me)Met-CH$_2$OMe;
H-L-Tyr-D-Ala-Gly-L-Phe(F)-L-(N-Et)Met-CH$_2$OMe;
H-L-Tyr-D-Ala-Gly-L-Phe(F)-L-(N-Me)Met-CH$_2$OEt;
H-L-Tyr-D-Ala-Gly-L-(N-Et)Phe(F)-L-Met-CH$_2$OEt;
H-L-Tyr-D-Ala-Gly-L-Phe(F)-L-(N-Me)Nle-CH$_2$OMe;
H-L-Tyr-D-Ala-Gly-L-Phe(F)-L-(N-Et)Pgl-CH$_2$OPr;
H-L-Tyr-D-Ala-Gly-L-Phe(F)-L-(N-Pr)Leu-CH$_2$OMe;
H-L-Tyr-D-Ala-Gly-L-(N-Al)Phe(F)-L-Met-CH$_2$OIp;
H-L-Tyr-D-Ala-Gly-L-(N-Me)Phe(F)-L-Met-OMe;
H-L-Tyr-D-Ala-Gly-L-Phe(F)-L-(N-Me)Met-OEt;
H-L-Tyr-D-Abu-Gly-L-Phe(F)-L-(N-Et)Met-OMe;
H-L-Tyr-D-Abu-Gly-L-Phe(F)-D-(N-Me)Met-OMe;
H-L-Tyr-D-Nva-Gly-L-Phe(F)-L-(N-Me)Met-OPr;
H-L-Tyr-D-Nva-Gly-L-(N-Et)Phe(F)-L-Met-OIp;
H-L-Tyr-D-Val-Gly-L-Phe(F)-D-(N-Et)Met-OMe;
H-L-Tyr-D-Val-Gly-L-(N-Pr)Phe(F)-L-Met-OEt;
H-L-Tyr-D-Nle-Gly-L-Phe(F)-L-(N-Bu)Met-OEt;
H-L-Tyr-D-Nle-Gly-L-Phe(F)-D-(N-Et)Gly-OMe;
H-L-Tyr-D-Leu-Gly-L-(N-Ip)Phe(F)-L-Met-OEt;
H-L-Tyr-D-Leu-Gly-L-Phe(F)-L-(N-Pr)Met-OPr;
H-L-Tyr-D-Ile-Gly-L-Phe(F)-L-(N-Bu)Met-OMe;
H-L-Tyr-D-Ile-Gly-L-Phe(F)-D-(N-Pr)Met-OMe;
H-L-Tyr-D-Ala-Gly-L-Phe(F)-L-(N-Et)Met-OMe;
H-L-Tyr-D-Ala-Gly-L-Phe(F)-L-(N-Pr)Met-OEt;
H-L-Tyr-D-Ala-Gly-L-Phe(F)-D-(N-Pr)Met(O$_2$)-OIp;
H-L-Tyr-D-Ala-Gly-L-(N-i-Bu)Phe(F)-L-Met-OMe;
H-L-Tyr-D-Ala-Gly-L-Phe(F)-L-(N-Bu)Met-OMe;

H-L-Tyr-D-Ala-Gly-L-(N-s-Bu)Phe(F)-D-Met-OEt;
H-L-Tyr-D-Ala-Gly-L-Phe(F)-L-(N-Me)Ala-OPr;
H-L-Tyr-D-Ala-Gly-L-Phe(F)-L-(N-Me)Abu-OIp;
H-L-Tyr-D-Ala-Gly-L-Phe(F)-L-(N-et)Nva-OMe;
H-L-Tyr-D-Ala-Gly-L-Phe(F)-D-(N-Et)Val-OMe;
H-L-Tyr-D-Val-Gly-L-Phe(F)-L-(N-Me)Nle-OMe;
H-L-Tyr-D-Leu-Gly-L-Phe(F)-L-(N-Me)Leu-OEt;
H-L-Tyr-D-Val-Gly-L-Phe(F)-L-(N-Et)Ile-OMe;
H-L-Tyr-D-Leu-Gly-L-Phe(F)-D-(N-Me)Ahp-OEt;
H-L-Tyr-D-Ala-Gly-L-(N-Cp)Phe(F)-L-Nle-OPr;
H-L-Tyr-D-Ala-Gly-L-Phe(F)-L-(N-Et)Hse(Me)-OIp;
H-L-Tyr-D-Ala-Gly-L-Phe(F)-L-(N-Me)Hle-OMe;
H-L-Tyr-D-Ala-Gly-L-Phe(F)-D-(N-Me)Hse(Me)-OMe;
H-L-Tyr-D-Ala-Gly-L-(N-Al)Phe(F)-L-Met-OEt;
H-L-Tyr-D-Gly(Al)-Gly-L-Phe(F)-L-(N-Me)Met-OEt;
H-L-Tyr-D-Gly(Cp)-Gly-L-Phe(F)-L-(N-Me)-Hil-OPr;
H-L-Tyr-D-Met-Gly-L-Phe(F)-L-(N-Me)Met-OMe;
H-L-Tyr-D-Cys(Me)-Gly-L-Phe(F)-D-(N-Et)Met-OPr;
H-L-Tyr-D-Met(O)-Gly-L-Phe(F)-L-(N-Et)Met-OIp;
H-L-Tyr-D-Cys(Me)(O)-Gly-L-Phe(F)-L-(N-Me)Npg-OMe;
H-L-Tyr-D-Ser-Gly-L-Phe(F)-L-(N-Me)Hse(Me)-OEt;
H-L-Tyr-D-Ala-Gly-L-(N-Et)-Phe(F)-L-Pgl-OEt;
H-L-Tyr-D-Ala-Gly-L-Phe(F)-L-(N-Me)Pgl-(OH)-OEt;
H-L-Tyr-D-Thr-Gly-L-(N-Et)Phe(F)-L-Met-OMe;
H-L-Tyr-D-Hse-Gly-L-Phe(F)-L-(N-Me)Met-OMe;
(N-Me)-L-Tyr-D-Ala-Gly-L-Phe(F)-L-(N-Me)Cys(-Me)-OMe;
H-L-Tyr-D-Ala-Gly-L-Phe(F)-L-(N-Me)-Cys(Me)(O)-OMe;
H-L-Tyr-D-Ala-Gly-L-Phe(F)-D-(N-Me)Cys(Et)-OMe;
(N-Et)-L-Tyr-D-Abu-Gly-L-Phe(F)-L-(N-Et)Nle-OEt;
H-L-Tyr-D-Val-Gly-L-(N-Et)Phe(F)-L-Hse(Me)-OMe;
(N-Pr)-L-Tyr-D-Leu-Gly-L-Phe(F)-L-(N-Me)-Cys(Et)(O)-OMe;
H-L-Tyr-D-Abu-Gly-L-Phe(F)-L-(N-Pr)Met(O)-OMe;
H-L-Tyr-D-Nle-Gly-L-Phe(F)-L-(N-Me)Eth-OEt;
H-L-Tyr-D-Ile-Gly-L-Phe(F)-D-(N-Pr)Eth(O)-OPr;
(N-Me)-L-Tyr-D-Leu-Gly-L-Phe(F)-L-(N-Et)-Nle-OIp;
(N-Me)-L-Tyr-D-Nva-Gly-L-Phe(F)-L-(N-Me)-Hse(Et)-OIp;
(N-Me)-L-Tyr-D-Ala-Gly-L-(N-Et)Phe(F)-D-Ser(-Me)-OPr;
H-L-Tyr-D-Ala-Gly-L-(N-Me)Phe(F)-L-Ser(Et)-OMe;
H-L-Tyr-D-Ala-Gly-L-(N-Me)Phe(F)-D-Leu-OEt;
H-L-Tyr-D-Ala-Gly-L-(N-Et)Phe(F)-L-Pgl-OMe;
H-L-Tyr-D-Ala-Gly-L-(N-Al)Phe(F)-L-Leu-OMe;
H-L-Tyr-D-Ala-Gly-L-(N-Pr)Phe(F)-L-Pgl(OH)-OMe;
H-L-Tyr-D-Ala-Gly-L-(N-Me)Phe(F)-L-Met-OMe;
H-L-Tyr-D-Ala-Gly-L-(N-Et)Phe(F)-L-Met($O_2$)-OMe;
and the like.

The compounds of this invention are prepared by routine methods for peptide synthesis. It is possible, during the synthesis of certain of the compounds of this invention, that partial racemization can occur. However, the extent of racemization, should such occur, is not sufficient to significantly alter the analgesic activity of the compounds of this invention.

The compounds of this invention can be synthesized by solid phase peptide synthesis or by classical solution phase synthesis. In the solid phase method, the peptide chain is sequentially constructed using a resin support, typically a benzhydrylamine resin or a chloromethylated polystyrene resin. The product is cleaved from the resin with HF and purified, generally chromatographically.

Whichever method is used, the preparation of the compounds of this invention involves the coupling of amino acids or peptide fragments by reaction of the carboxyl function of one with the amino function of another to produce an amide linkage. In order to effectively achieve coupling, it is desirable, first, that all reactive functionalities not participating directly in the reaction be inactivated by the use of appropriate blocking groups, and, secondly, that the carboxyl function which is to be coupled be appropriately activated to permit coupling to proceed. All of this involves a careful selection of both reaction sequence and reaction conditions as well as utilization of specific blocking groups so that the desired peptide product will be realized. Each of the amino acids which is employed to produce the compounds of this invention and which has the particularly selected protecting groups and/or activating functionalities is prepared by techniques well recognized in the peptide art.

Selected combinations of blocking groups are employed at each point of the total synthesis of the compounds of this invention. These particular combinations have been found to function most smoothly. Other combinations would operate in the synthesis of the compounds of this invention, although, perhaps, with a lesser degree of success. Thus, for example, benzyloxycarbonyl, t-butyloxycarbonyl, t-amyloxycarbonyl, p-methoxybenzyloxycarbonyl, adamantyloxycarbonyl, and isobornyloxycarbonyl can be variously employed as amino blocking groups in the synthesis of the compounds of this invention. Furthermore, benzyl (Bzl) generally is employed as the hydroxy-protecting group for the tyrosyl residue even though others, such as p-nitrobenzyl (PNB), p-methoxybenzyl (PMB), and the like, could well be employed.

The carboxyl blocking groups used in preparing the compounds of this invention can be any of the typical ester-forming groups, including, for example, methyl, ethyl, benzyl, p-nitrobenzyl, p-methoxybenzyl, 2,2,2-trichloroethyl, and the like.

Coupling of the suitably protected N-blocked amino acid or peptide fragment with a suitably protected carboxy-blocked amino acid or peptide fragment in preparation of the compounds of this invention consists of rendering the free carboxyl function of the amino acid or peptide fragment active to the coupling reaction. This can be accomplished using any of several well recognized techniques. One such activation technique involves conversion of the carboxyl function to a mixed anhydride. The free carboxyl function is activated by reaction with another acid, typically a derivative of carbonic acid, such as an acid chloride thereof. Examples of acid chlorides used to form mixed anhydrides are ethyl chloroformate, phenyl chloroformate, sec-butyl chloroformate, isobutyl chloroformate, pivaloyl chloride, and the like. Preferably, isobutyl chloroformate is employed.

Another method of activating the carboxyl function for the purpose of carrying out the coupling reaction is by conversion to its active ester derivative. Such active esters include, for example, a 2,4,5-trichlorophenyl ester, a pentachlorophenyl ester, a p-nitrophenyl ester, and the like. Another coupling method available for use is the well-recognized azide coupling method.

The preferred coupling method in preparation of the compounds of this invention involves the use of N,N'-dicyclohexylcarbodiimide (DCC) to activate the free carboxyl function thereby permitting coupling to proceed. This activation and coupling technique is carried out employing an equimolar quantity of DCC relative to the amino acid or peptide fragment and is carried out in the presence of an equimolar quantity of 1-hydroxybenzotriazole (HBT). The presence of HBT suppresses undesirable side reactions including the possibility of racemization.

Cleavage of selected blocking groups is necessary at particular points in the synthetic sequence employed in preparation of the compounds of this invention. A chemist of ordinary skill in the art of peptide synthesis can readily select from representative protecting groups those groups which are compatible in the sense that selective cleavage of the product can be accomplished permitting removal of one or more but less than all of the protecting groups present on the amino acid or peptide fragment. These techniques are well recognized in the peptide art. A fuller discussion of the techniques which are available for selective cleavage is provided in the literature in Schröder and Lübke, *The Peptides*, Volume I, Academic Press, New York, (1965), and especially in the Table provided at pages 72–75 thereof.

Cleavage of carboxyl protecting groups can be accomplished by alkaline saponification. Relatively strong alkaline conditions, typically using an alkali metal hydroxide, such as sodium hyroxide, potassium hydroxide, lithium hydroxide, and the like, are generally employed to deesterify the protected carboxyl. The reaction conditions under which saponification is accomplished are well recognized in the art. Many of the carboxyl blocking groups also can be removed by catalytic hydrogenolysis including, for example, hydrogenolysis in the presence of a catalyst such as palladium on carbon. Furthermore, in those instances in which the carboxyl blocking group is p-nitrobenzyl or 2,2,2-trichloroethyl, deblocking can be accomplished by reduction in the presence of zinc and hydrochloric acid.

Many of the amino blocking groups are cleaved by treating the protected amino acid or peptide with an acid such as formic acid, trifluoroacetic acid (TFA), p-toluenesulfonic acid (TSA), benzenesulfonic acid (BSA), naphthalenesulfonic acid, and the like, to form the respective acid addition salt product. Cleavage of others, for example, benzyloxycarbonyl, can be accomplished by treating the blocked amino acid or peptide with a mixture of HBr and acetic acid to produce the corresponding hydrobromide acid addition salt. The particular method or reagent which is employed will depend upon the chemical or physical characteristics of the materials involved in the specific deblocking reaction. The resulting acid addition salt can be converted to a more pharmaceutically acceptable form by treatment with a suitable ion exchange resin, such as DEAE Sephadex A25, Amberlyst A27, and the like.

The hydroxy-protecting group can be retained on the peptide throughout the sequence of its preparation, being removed during the final synthetic step in conjunction with cleavage of the amino blocking group. However, depending upon the conditions employed for removal of the carboxyl blocking group, it may be removed earlier in the preparative sequence. When the carboxyl group is cleaved by alkaline saponification, the hydroxy-protecting group is retained; however, when catalytic hydrogenolysis is employed for removal of the carboxyl protecting group, the hydroxy protecting group also is cleaved. The latter situation does not represent a serious problem since preparation of the compounds of this invention can be accomplished in the presence of a tyrosyl residue having a free hydroxyl group, for example, a tyrosyl residue.

Of the classical solution methods, a preferred specific method for preparing the compounds of this invention involves coupling a separately prepared N-terminal tripeptide with a separately prepared C-terminal dipeptide followed by appropriate deblocking of any remaining blocked moieties. The separately prepared C-terminal dipeptide which is reacted with the N-terminal tripeptide can be structured so as to contain the amide, alcohol, ether, or ester moiety. Alternatively, it can contain a group which represents a precursor to the desired C-terminal moiety. The general sequence, illustrating preparation of a pentapeptide of this invention, can be depicted as follows. In the sequence, the letter Z represents the C-terminal moiety, whether in its final form or as a precursor, the symbol AA represents an amino acid residue, and the number appended to the symbol AA represents the position of the amino acid in the ultimate peptide product sequence.

BOC—D—(AA)$_2$—OH + H—Gly—OBZL

↓ IBCF
  NMM
  −15° C.

BOC—D—(AA)$_2$—Gly—OBzl

↓ HCl/HOAc

Cl$^-$H$_2^+$—D—(AA)$_2$—Gly—OBzl

↓ neutralize

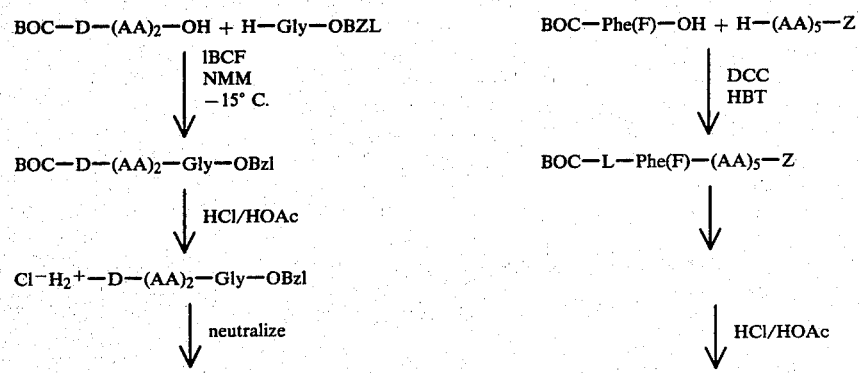

BOC—L—Tyr(OBzl)—OH + H—D—(AA)₂—Gly—OBzl

| IBCF
| NMM
| −15° C.
↓

BOC—L—Tyr(OBzl)—D—(AA)₂—Gly—OBzl

| H₂
| PD/C
↓

BOC—L—Tyr—D—(AA)₂—Gly—OH

-continued

Cl⁻H₂⁺—L—Phe(F)—(AA)₅—Z

↓ neutralize

H—L—Phe(F)—(AA)₅—Z

| DCC
| HBT
↓

BOC—L—Tyr—D—(AA)₂—Gly—L—Phe(F)—(AA)₅—Z

| (1) TFA
| (2) Reversed-Phase Liquid
|     Chromatography over C₁₈—silica
| (3) Sephadex G-10
↓

AcOH.H—L—Tyr—D—(AA)₂—Gly—L—Phe(F)—(AA)₅—Z

The above represents only one sequence for preparing compounds of this invention. Other sequences are available. Another solution method which can be employed involves the step-wise, sequential addition of single amino acids in construction of the peptide chain beginning with the C-terminal amino acid moiety. Reaction techniques such as those described above are employed in this as well as any other contemplated preparative sequence.

In certain of the compounds of this invention, one or more of the groups $R_1$, $R_3$, and $R_5$ are, variously, alkyl, allyl, or cyclopropylmethyl. In these instances, the appropriate N-substituted amino acid is employed in the preparative sequence. Any of the N-monosubstituted amino acids can be prepared as follows using an N-protected amino acid as starting material:

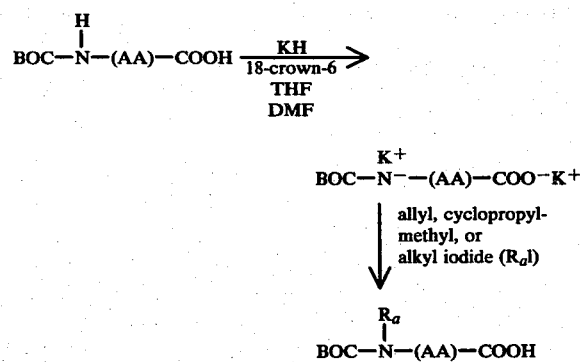

As the above sequence indicates, the amino acid first is treated with potassium hydride in the presence of a suitable crown ether to generate the dianion. The intermediate then is treated with the appropriate allyl, cyclopropylmethyl, or alkyl iodide to obtain the desired N-substituted amino acid.

It will be apparent to those of ordinary skill in the art of peptide synthesis that racemization at the α-carbon can occur under strongly alkaline conditions such as those employed in the above alkylation procedure. The degree of racemization may vary depending upon the particular amino acid which is involved. Racemization can be minimized by using excess alkylating agent and by keeping the reaction time as short as possible. Nevertheless, even in the event that excessive racemization does occur, the product can be purified by recrystallization as the salt of a suitable chiral amine, for example, as the salt of d(+) α-phenylethylamine.

The C-terminal portion of the peptides of this invention is derivatized to its primary or secondary amide, ester, alcohol, or ether. In the amide pentapeptides of this invention, the amide is unsubstituted or N-monosubstituted. Derivatization to the amide is accomplished by activation of the carboxyl group of the amino acid with N,N'-dicyclohexylcarbodiimide (DCC) in the presence of 1-hydroxybenzotriazole (HBT) to give the HBT ester. In producing the pentapeptides of this invention, the ester then is reacted with anhydrous ammonia or the appropriate primary amine to give the unsubstituted or N-monosubstituted amide. Suitable primary amines for preparation of the pentapeptides of this invention include methylamine, ethylamine, n-propylamine, and isopropylamine.

The C-terminal esters are available from the corresponding acids by techniques well recognized in the art. Derivatization to the primary alcohol is achieved by preparing the methyl ester of the C-terminal amino acid or peptide. The ester then is reduced using sodium borohydride and lithium chloride to give the corresponding primary alcohol derivative.

The ethers can be prepared by any of a variety of well-recognized methods. One involves treating the corresponding alcohol in an aqueous sodium hydroxide medium with an alkyl bromide in which the alkyl group corresponds to the intended alkyl portion of the ether product.

The compounds of this invention are valuable pharmaceutical agents. They exhibit analgesic activity and also neuroleptic activity. They are especially useful in alleviation of pain and amelioration of emotional disturbances when administered parenterally or orally to mammals, including humans.

The compounds of this invention may be administered alone or in combination with pharmaceutically acceptable carriers, the proportion of which is determined by the solubility and chemical nature of the compound, the selected route of administration, and standard pharmaceutical practice.

Preferred compositions are those suitable for parenteral administration, that is, intramuscular, subcutaneous, or intravenous. These include sterile, injectable solutions or suspensions, and sterile injectable depot or slow-release formulations. Particularly convenient sterile, injectable solutions are made up in isotonic saline or isotonic dextrose. The sterile, injectable compositions can be prepared and stored as such or they can be prepared immediately prior to use by adding a sterile medium, for example, water, to a known weight of sterile ingredient enclosed in a vehicle, for example, a vial or an ampoule, which maintains sterility of the ingredient. The known weight of sterile ingredient may also contain sufficient sterile dextrose or sodium chloride to provide an isotonic solution or suspension after addition of the sterile medium.

Preferred compositions also are those suitable for oral administration. These can be prepared as discrete units such as capsules, tablets, and the like, each containing a predetermined amount of the active ingredient. Moreover, they, for example, can be prepared in powder or granule form, as a solution or a suspension in an aqueous or a non-aqueous medium, or as an emulsion.

The tablet can be prepared by compression, generally with one or more accessory ingredients. The tablets are prepared by compressing the active ingredient in a free-flowing form, such as a powder or granule, and generally mixed with one or more other ingredients, such as binders, lubricants, inert diluents, lubricating agents, surface active agents, buffers, flavoring agents, thickeners, preservatives, dispersing agents, and the like.

Physicians will determine the particular dosage of the compounds of this invention which is most suitable. The selected dosages will vary depending upon the mode of administration, the particular compound administered, the patient under treatment, and the kind of treatment. In general, however, the dosage will range from about 10 $\mu$g. to about 2 mg. per kilogram body weight of the recipient, and, preferably, from about 100 $\mu$g. to about 500 $\mu$g. per kilogram body weight, when administered intramuscularly or subcutaneously, and from about 1 $\mu$g. to about 200 $\mu$g. per kilogram body weight of the recipient, and, preferably, from about 3 $\mu$g. to about 50 $\mu$g. per kilogram body weight, when administered intravenously. When administered orally, the dosage generally will range from about 1 mg. to about 500 mg. per kilogram body weight of the recipient, and, preferably, from about 50 mg. to about 200 mg. per kilogram body weight, and, more preferably, from about 50 mg. to about 100 mg. per kilogram body weight.

The following examples are provided to illustrate the preparation and activity of the compounds of this invention. They are not intended to be limiting upon the scope thereof.

EXAMPLE 1

Preparation of
L-Tyrosyl-D-alanylglycyl-L-p-fluorophenylalanyl-L-($N^\alpha$-methyl)methioninamide, Acetate Salt.

A. Trifluoroacetic Acid Salt of
L-Tyrosyl-D-alanyl-glycyl-D,L-p-fluorophenylalanyl-L-($N^\alpha$-methyl)methionyl Benzhydrylamine Resin.

The peptide-resin was synthesized by automated solid-phase synthesis in a Beckman 990 Peptide Synthesizer using four grams of benzhydrylamine resin (Beckman, 0.47 mmoles-N/gram). The resin was neutralized with four percent diisopropylethylamine (DIEA) in methylene chloride and then was allowed to couple with Boc-(N-Me)Met-OH and DCC in methylene chloride to give the Boc-(N-Me)-Met-substituted resin. Boc-D,L-(p-F)PheOH, Boc-Gly-OH, Boc-D-Ala-OH, and Boc-Tyr-OH were successively incorporated onto the peptide-resin by initial coupling according to Program No. 1 and subsequent recoupling of the same amino acid according to Program No. 2. The resulting Boc-pentapeptide-resin was deprotected according to Steps 1–8 of Program No. 1 to give 4.98 grams of the title compound. The washes in Programs Nos. 1 and 2 were carried out at 8 ml. per gram resin.

Program No. 1
1. Wash three times with $CH_2Cl_2$.
2. Treat for five minutes with a 30:5:65 volume mixture of $TFA:Et_3SiH:CH_2Cl_2$.
3. Treat as in Step 2 for 30 minutes.
4. Wash twice with $CH_2Cl_2$.
5. Wash with methanol:$CH_2Cl_2$ (1:1).
6. Wash twice with methanol.
7. Wash with methanol:$CH_2Cl_2$ (1:1).
8. Wash twice with $CH_2Cl_2$.
9. Treat four times for two minutes each with 4% DIEA in $CH_2Cl_2$.
10. Repeat Steps 4 to 8.
11. Treat with 2.5 equivalents of the desired amino acid derivative in $CH_2Cl_2$ and 1.25 equivalents of DCC in $CH_2Cl_2$ for 120 minutes.
12. Wash four times with $CH_2Cl_2$.
13. Repeat Steps 5 to 7.
14. Wash three times with $CH_2Cl_2$.

Program No. 2
1. Treat four times for two minutes each with 4% DIEA in $CH_2Cl_2$.
2. Wash twice with $CH_2Cl_2$.
3. Wash with methanol:$CH_2Cl_2$ (1:1).
4. Wash twice with methanol.
5. Wash with methanol:$CH_2Cl_2$ (1:1).
6. Wash twice with $CH_2Cl_2$.
7. Wash three times with DMF:$CH_2Cl_2$ (1:1).
8. Treat with 2.5 equivalents of the desired amino acid derivative in DMF:$CH_2Cl_2$ (1:1) and 1.25 equivalents of DCC in $CH_2Cl_2$ for 120 minutes.
9. Wash four times with DMF:$CH_2Cl_2$ (1:1).
10. Repeat Steps 4 to 6.

B. Hydrogen Fluoride Salt of L-Tyrosyl-D-alanyl-glycyl-D,L-p-fluorophenylalanyl-L-($N^\alpha$-methyl)methioninamide.

The peptide resin from Part A was reacted with liquid anhydrous HF in vacuo for 60 minutes at 0° C. with anisole as scavenger. The volatile components were removed from the reaction in vacuo, and the peptide-resin was triturated with ether and filtered to removed residual HF and anisole. The peptide was extracted from the resin by trituration with 10 percent acetic acid. The 10 percent acetic acid extract was lyophilized to yield 745 mg. of crude title compound.

C. Chromatographic Purification to Obtain Final Product

The crude mixture of peptide diastereomers was chromatographed over a column (5×72 cm.) of reverse-phase ($C_{18}$) silica gel at low pressure (75–80 psig) with 26 percent acetonitrile in 0.1 N ammonium acetate. After collecting 2,000 ml. of eluant, 1.5 minute fractions of 17.0 ml. each were collected. Fractions 36–65 were pooled and lyophilized to give the final product, and Fractions 78–110 were pooled and lyophilized to give the corresponding D-p-fluorophenylalanyl compound. Both products were chromatographed separately over a Sephadex G-10 colum (2.5×100 cm.) in 0.2 N acetic acid to remove ammonium acetate. The fraction were lyophilized to give the peptides as amorphous, white solids.

(1) L-p-fluorophenylalanyl compound (253.8 mg.) $[\alpha]_D^{25}+14.4$ (c=0.5, 1 N HCl).

$[\alpha]_{365}^{25}+57.8$ (c=0.5, 1 N HCl).

Analysis, Calculated for $C_{31}H_{43}FN_6O_8S$ (678.876): C, 54.85; H, 6.39; N, 12.38; F, 2.80. Found: C, 55.05; H, 6.17; N, 12.62; F, 3.07.

Amino Acid Analysis:

|  | Gly | Ala | Tyr | NH3 | Phe(F) | % Peptide |
|---|---|---|---|---|---|---|
| (1) | 0.99 | 1.00 | 1.00 | 0.98 | 1.03 | 97.1 |
| (2) | 1.01 | 1.00 | 1.00 | 1.00 | 1.05 | 96.8 |

(2) D-p-fluorophenylalanyl compound (223.1 mg) $[\alpha]_D^{25}+5.14$ (c=0.5, HCl).

Analysis, Calculated for $C_{31}H_{43}FN_6O_8S$ (678.876): C,54.85; H, 6.39; N, 12.38; F, 2.80. Found: C, 54.62; H, 6.58; N, 12.59; F, 2.49.

Amino Acid Analysis:

|  | Gly | Ala | Tyr | NH3 | PHe(F) | % Peptide |
|---|---|---|---|---|---|---|
| (1) | 1.00 | 1.00 | 1.01 | 0.99 | 1.04 | 95.2 |
| (2) | 0.99 | 1.00 | 1.00 | 1.00 | 1.03 | 96.4 |

EXAMPLE 2

Preparation of L-Tyrosyl-D-alanylglycyl-L-p-fluorophenylalanyl-L-p-methoxyphenylglycinamide, Acetate Salt.

A. Boc-L-p-methoxyphenylglycinamide

To 50 ml. of tetrahydrofuran (THF) were added 5.03 grams (17.9 mmoles) of Boc-p-methoxyphenylglycine. The mixture was chilled in an acetone-ice bath to −9° C. To the mixture then were added 1.99 ml. (17.9 mmoles) of N-methylmorpholine and 2.34 ml. (17.9 mmoles) isobutyl chloroformate. The mixture was stirred for 2.5 minutes. Ammonia was bubbled into the chilled reaction mixture for one hour. Distilled water (80 ml.) was added to the mixture, and the mixture was extracted with 80 ml. of ethyl acetate. The ethyl acetate extract then was washed successively with 1 N potassium bicarbonate, 1 N hydrochloric acid, and water. The ethyl acetate extract was dried over anhydrous magnesium sulfate, filtered, and evaporated to give 4.77 grams of a white solid which was recrystallized from a mixture of ethyl acetate and petroleum ether to give 3.32 grams (49%).

B. L-p-Methoxyphenylglycinamide, hydrochloride salt

To 32 grams (12.0 mmoles) of the product from Part A in 6.0 ml. of glacial acetic acid were added 4.7 ml. of triethylsilane and 4.7 ml. of anisole. To the mixture then were added 47 ml. (3 equivalents) of a 0.77 N HCl/acetic acid solution. The mixture was stirred at room temperature for 35 minutes. Ether (600 ml.) was added, and the resulting white precipitate was triturated. The mixture was filtered, and the collected precipitate was washed with ether to give 2.53 grams (66%) of the title compound.

C. $N^\alpha$-t-Butyloxycarbonyl-D,L,p-fluorophenylalanyl-L-p-methoxyphenylglycinamide.

To a suspension of the compound from Part B (0.65 grams; 3 mmoles) in 8.0 ml. of cold (0° C.) DMF was added DIEA (0.52 ml.; 3 mmoles). A solution of Boc-D,L-(p-F)Phe-OH (0.85 grams; 3 mmoles) in DMF (8.0 ml.) then was added to the mixture followed by HBT (0.81 grams; 6 mmoles) and a solution of DCC (0.62 grams; 3 mmoles) in DMF (4 ml.). The resulting mixture was stirred under a $CaSO_4$ drying tube at 0° C. for 1.5 hours and then at room temperature for 16 hours. The mixture was filtered to remove dicyclohexylurea (DCU), and the filtrate was evaporated in vacuo to give a yellow residue. The residue was partitioned between ethyl acetate (300 ml.) and water (200 ml.), and the layers were separated. The ethyl acetate layer was washed with pH 10 buffer (3×300 ml.), 0.1 N HCl (3×300 ml.), and water (300 ml.). The ethyl acetate was dried over magnesium sulfate, filtered, and the solvent was removed in vacuo to give 1.44 grams (100%) of the title compound. The material showed the presence of DCU by thin-layer chromatography (tlc).

D. D,L-p-Fluorophenylalanyl-L-p-methoxyphenylglycinamide

To a solution of the compound from Part D in acetic acid (4 ml.) were added anisole (1.0 ml.), triethylsilane (1.0 ml.), and 1.54 N HCl in acetic acid (10 ml.). The solution was stirred under a $CaSO_4$ drying tube at room temperature (30 minutes) and then was diluted with ether (600 ml.). The resulting precipitate was filtered, washed with ether (2×25 ml.) and dried in vacuo at 35° C. to give 1.10 grams (96%) of the title compound. The compound was shown to be pure by tlc analysis.

E. L-Tyrosyl-D-alanyl-glycyl-D,L-p-fluorophenylalanyl-L-p-methoxyphenylglycinamide, Trifluoroacetate Salt.

To a suspension of the product from Part D (1.10 grams; 2.89 mmoles) in 9 ml. of cold (0° C.) DMF was added Boc-L-Tyr-D-Ala-Gly-OH, dicyclohexylamine salt (1.70 grams; 2.88 mmoles) suspended in 21 ml. of DMF. To the resulting stirred mixture were added HBT (770 mg.; 5.76 mmoles) and a solution of DCC (594 mg.; 2.88 mmoles) in 2.5 ml. of DMF. The resulting mixture was stirred at 0° C. for 1.25 hours and then at room temperature for 16 hours. The mixture was filtered to remove DCU, and the filtrate was concentrated in vacuo to give yellow residue. To the residue were added anisole (6.0 ml.), triethylsilane (6.0 ml.), and trifluoroacetic acid (60 ml.). The resulting solution was stirred under a $CaSO_4$ drying tube at room temperature for 0.5 hours after which the reactin mixture was concentrated in vacuo to a yellow oil. Ether (1.5 liters) was added to the yellow oil, and the resulting precipitate was collected by filtration and dried in vacuo to give 2.01 grams (93 percent) of crude title compound.

F. Chromatographic Purification to Obtain Final Product

The product from Part E was treated in the manner described in Part C of Example 1 to separate the two diastereomers and to obtain 763 mg. of the title compound.

$[\alpha]_D^{25} +67.06°$ (c=0.375, 75% 1 N HCl:25% DMF).

$[\alpha]_{365}^{25} +263.88°$ (c=0.375, 75% 1 N HCl:25% DMF).

Analysis, Calculated for $C_{34}H_{41}FN_6O_9$(696.738): C, 58.61; H, 5.93; N, 12.06; F, 2.73. Found: C, 58.90; H, 6.03; N, 12.34; F, 2.53.

Amino Acid Analysis: Gly, 1.00; Ala, 1.00; Tyr, 0.99; Pgl(MeO), 1.04; Phe(F), 0.89; NH₃, 0.99; %Peptide, 90.

EXAMPLE 3

Preparation of
L-Tyrosyl-D-alanyl-glycyl-L-p-fluorophenylalanyl-L-phenylglycinamide, Acetate Salt, and
L-Tyrosyl-D-alanyl-glycyl-L-p-fluorophenylalanyl-D-phenylglycinamide, Acetate Salt.

These products were prepared in accordance with the procedure of Example 2 and exhibited the following characteristics.

(1) L-phenylglycinamide compound (1.043 g.)

$[\alpha]_D^{25} +90.72°$ (c=0.5, 1 N HCl).

$[\alpha]_{365}^{25} +333.33°$ (c=0.5, 1 N HCl).

Analysis, Calculated for $C_{33}H_{39}FN_6O_8$(666.712): C, 59.45; H, 5.90; N, 12.61; F, 2.85. Found: C, 59.25; H, 6.09; N, 12.43; F, 3.08.

Amino Acid Analysis: Gly, 1.01; Ala, 1.00; Tyr, 1.00; Pgl, 0.99; Phe(F), 0.98; NH₃, 1.01; %Peptide, 90.

(2) D-phenylglycinamide compound (626 mg.)

$[\alpha]_D^{25} +17.50°$ (c=0.5, 1 N HCl).

$[\alpha]_{365}^{25} +79.76$ (c=0.5, 1 N HCl).

Analysis, Calculated for $C_{33}H_{39}FN_6O_8$(666.712): C, 59.45; H, 5.90; N, 12.61; F, 2.85. Found: C, 59.46; H, 5.88; N, 12.35; F, 2.68.

Amino Acid Analysis: Gly, 0.99 Ala, 1.00, Tyr, 0.96; Pgl, 1.02; Phe(F), 1.00; NH₃, 1.05; %Peptide, 88.

EXAMPLE 4

Preparation of
L-Tyrosyl-D-threonylglycyl-L-p-fluorophenylalanyl-L-(Nα-methyl)methioninamide, Acetate Salt This product was prepared in accordance with the procedure of Example 1 to obtain 216 mg. which exhibited the following characteristics.

$[\alpha]_D^{25} +14.99°$ (c=0.5, 1 N HCl).

$[\alpha]_{365}^{25} +51.28°$ (c=0.5, 1 N HCl).

Analysis, Calculated for $C_{32}H_{45}FN_6O_9S$(708.813): C, 54.23; H, 6.40; N, 11.86; F, 2.86. Found: C, 54.47; H, 6.28; N, 11.91; F, 2.51.

Amino Acid Analysis: Thr, 0.98; Gly, 1.00; Tyr, 1.03; Phe(F), 0.96; NH₃, 1.27; %Peptide, 86.

The analgesic activity of the compounds of this invention is demonstrated by the mouse hot plate test. In this test, a mouse is placed inside an upright acrylic cylinder comprising, as its base, a hot plate surface which is maintained at 52° C. The mouse is given, orally or by subcutaneous injection, a predetermined amount of test compound dissolved or suspended in a suitable carrier, and, 15 minutes after administration of the test compound, the mouse is placed on the hot plate surface. The latency in seconds until the mouse jumps from the hot plate surface is measured. An agent which exhibits analgesic activity produces an increase in this latency over that of control mice which receive only the carrier. This must occur in a dose range which produces no motor incoordination or incapacitation. The following Table records the ED₅₀ results obtained from this test.

TABLE

| Analgesic Activity, Hot Plate Test | |
|---|---|
| Compound | ED₅₀, mg./kg., subcutaneous |
| Example 1 | 0.023 |
| Example 2 | 1.04 |
| Example 3 | |
| L-Pgl | 0.063 |
| D-Pgl | 0.103 |
| Example 4 | 0.088 |

We claim:

1. A compound of the formula

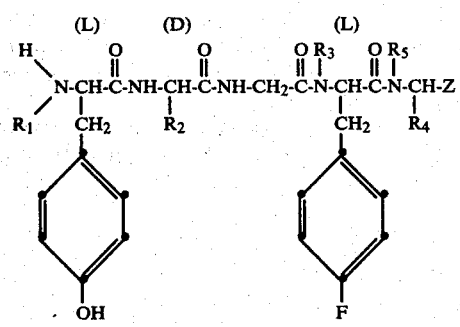

and pharmaceutically acceptable non-toxic acid addition salts thereof, in which

L and D define the chirality;

$R_1$ is hydrogen or $C_1$-$C_3$ primary alkyl;

$R_2$ is $C_1$-$C_4$ primary or secondary alkyl, allyl, cyclopropylmethyl, $C_1$-$C_2$ hydroxyalkyl, or —(CH₂)ₘ—U—CH₃ in which U is —S— or

and m is 1 or 2;

$R_3$ is hydrogen, $C_1$-$C_4$ primary or secondary alkyl, cyclopropylmethyl, or allyl;

$R_4$ is phenyl, or monosubstituted phenyl in which the substituent is halo, hydroxy, $C_1$-$C_3$ alkoxy, nitro, $C_1$-$C_3$ alkyl, or trifluoromethyl;

$R_5$ is hydrogen; and

Z is —CH₂OR₆,

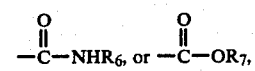

in which $R_6$ is hydrogen or $C_1$-$C_3$ alkyl and $R_7$ is $C_1$-$C_3$ alkyl.

2. Compound of claim 1, in which $R_1$ is hydrogen.

3. Compound of claim 1, in which $R_2$ is $C_1$-$C_4$ primary or secondary alkyl.

4. Compound of claim 3, in which $R_2$ is methyl.

5. Compound of claim 1, in which $R_2$ is $C_1$-$C_2$ hydroxyalkyl.

6. Compound of claim 1, in which $R_3$ is $C_1$-$C_4$ primary or secondary alkyl.

7. Compound of claim 6, in which $R_3$ is methyl or ethyl.

8. Compound of claim 1, in which $R_4$ is phenyl or p-hydroxyphenyl.

9. Compound of claim 1, in which Z is $-CH_2OR_6$ and $R_6$ is hydrogen.

10. Compound of claim 1, in which Z is

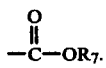

11. Compound of claim 1, in which Z is

12. Compound of claim 11, in which $R_6$ is hydrogen.
13. Compound of claim 12, in which $R_1$ is hydrogen.
14. Compound of claim 12, in which $R_4$ is phenyl or monosubstituted phenyl.
15. Compound of claim 14, in which $R_1$ is hydrogen.
16. Compound of claim 15, in which $R_2$ is $C_1-C_2$ hydroxyalkyl.
17. Compound of claim 15, in which $R_2$ is $C_1-C_4$ primary or secondary alkyl.
18. Compound of claim 17, in which $R_2$ is methyl.
19. Compound of claim 18, in which the chirality of the amino acid residue in Position 5 is L-.
20. Compound of claim 19, in which $R_3$ is hydrogen.
21. Compound of claim 20, in which $R_4$ is phenyl.
22. Compound of claim 20, in which $R_4$ is p-methoxyphenyl.
23. Compound of claim 12, in which $R_1$ is $C_1-C_3$ primary alkyl.
24. Compound of claim 23, in which $R_1$ is methyl.
25. Compound of claim 24, in which $R_4$ is phenyl or monosubstituted phenyl and $R_3$ is hydrogen.
26. Compound of claim 25, in which the chirality of the amino acid residue in Position 5 is L-.
27. Compound of claim 26, in which $R_2$ is methyl.
28. Compound of claim 27, in which $R_4$ is phenyl.
29. Compound of claim 27, in which $R_4$ is p-methoxyphenyl.

* * * * *